United States Patent [19]

Gaffar et al.

[11] 4,041,149

[45] Aug. 9, 1977

[54] COMPOSITION AND METHOD OF CONTROLLING AND PREVENTING MOUTH ODOR

[75] Inventors: Maria Corazon Gaffar; Abdul Gaffar, both of Somerset; John P. Hauschild, Sommerville, all of N.J.

[73] Assignee: Colgate-Palmolive Company, New York, N.Y.

[21] Appl. No.: 648,231

[22] Filed: Jan. 12, 1976

[51] Int. Cl.² .............................................. A61K 7/16
[52] U.S. Cl. ...................................... 424/57; 424/128
[58] Field of Search .............................. 424/57; 8/111

[56] References Cited

U.S. PATENT DOCUMENTS 3,666,399   5/1972   Castrantas ................................. 8/111

Primary Examiner—Lewis Gotts
Assistant Examiner—Cary Owens
Attorney, Agent, or Firm—Herbert S. Sylvester

[57] ABSTRACT

A method of preventing and controlling mouth odor which comprises applying a novel oral composition containing an effective amount of a peroxydiphosphate salt to the oral cavity, wherein the peroxydiphosphate salt is activated by the salivary phosphatases to slowly and continuously generate hydrogen peroxide which deodorizes the oral cavity.

9 Claims, No Drawings

COMPOSITION AND METHOD OF CONTROLLING AND PREVENTING MOUTH ODOR

This invention relates to a novel composition and the method of treating the oral cavity in order to prevent and control mouth odor by eliminating odoriferous substances in the oral cavity.

Mouth odor has been attributed to the presence of volatile sulfur compounds such as hydrogen sulfide, methyl mercaptan and dimethyl sulfide, resulting from putrefactive processes occurring in the oral cavity. Aforesaid volatile sulfur compounds have been detected both in vivo from mouth air samples; and in vitro from an incubated saliva system and appropriate substrates by an instrumental GC-flame photometric technique.

Heretofore, antimicrobial agents were utilized in oral compositions to act on the microorganisms responsible for oral putrefactive processes, thereby preventing the formation of volatile sulfur compounds. A serious disadvantage in the use of antibacterial agents in oral compositions has been their general propensity to stain the teeth.

Accordingly, it is an object of this invention to provide an oral composition containing a non-staining, non-antimicrobial mouth odor inhibitor.

Another object of instant invention is to provide a stable (good shelf-life) oral composition effective in inhibiting mouth odor over a protracted period of time.

It has been found that oxidizing agents act on the odoriferous volatile sulfur compounds to form non-odoriferous sulfur compounds. Accordingly an effective method of controlling mouth odor entails the use of an oral composition containing an oxidizing agent. Hydrogen peroxide, which is a well known oxidizing agent, causes undesirable effects in the oral cavity such as black, hairy tongue and irritation of the oral mucous membranes. In addition, hydrogen peroxide is unstable in mouth rinse formulations.

Accordingly, it has now been found that tetrapotassium peroxydiphosphate ($K_4P_2O_8$) is an oxidizing agent which slowly releases hydrogen peroxide in the presence of phosphatase enzymes found in saliva in accordance with the following equation:

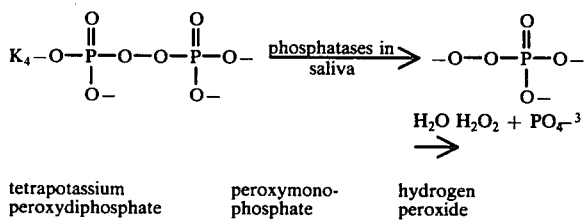

| tetrapotassium peroxydiphosphate | peroxymono-phosphate | hydrogen peroxide |

It slowly oxidizes the —SH groups of proteins to —S—S. Since the presence of —SH groups in proteins (or amino acids) provide substrates for the sulfur volatiles involved in mouth odor, this compound should inhibit mouth odor via interactions with the substrate.

In addition, the peroxydiphosphate is substantive to oral surfaces and binds or reacts with the enamel surfaces of the teeth, i.e., the $Ca^{++}$ ions of the enamel, to provide for a longer lasting effect. The peroxydiphosphate has no initial burst effect of $H_2O_2$ which leads to black, hairy tongue, because it releases $H_2O_2$ at a slower rate. At equivalent concentrations of the peroxydiphosphate compound and hydrogen peroxide, it has one-tenth the amount of available oxygen compared to hydrogen peroxide, yet it is more effective in preventing odor by controlling the formation of volatile sulfur compounds, than $H_2O_2$. It is substantially non-irritating to the oral mucosa, as well as non-toxic. It is stable in oral formulations and said compositions are effective in inhibiting odor in vitro even after four months of aging; whereas $H_2O_2$ loses 50% of its effectiveness after only 24 hours incubation. In addition, the peroxydiphosphate salt exhibits no potential for staining teeth, which is an undesirable property of anti-bacterial compounds such as the quaternary ammonium compounds. Oral compositions such as mouthrinses containing the peroxydiphosphate compounds have the same potential for plaque reduction and gingival health improvement as the peroxide containing mouthrinses (i.e., Gly-Oxide).

The tetrapotassium peroxydiphosphate is a stable, odorless, finely divided, free-flowing, white, non-hygroscopic crystalline solid having a molecular weight of 346.35 and an active oxygen content of 4.6%. The potassium peroxydiphosphate is 47–51% water-soluble at 0°–61° C, but insoluble in common solvents such as acetonitrile, alcohols, ethers, ketones, dimethyl formamide, dimethyl sulfoxide, and the like. A 2% aqueous solution has a pH of about 9.6 and a saturated solution thereof a pH of about 10.9. A 10% solution in water at 25° C showed no active oxygen loss after four months; and at 50° C a 10% solution showed an active oxygen loss of 3% in 6 months. This stability permits long shelf-life of oral compositions containing said peroxydiphosphate compound.

In addition, the unusual stability of the peroxydiphosphate in aqueous solution requires the addition of the phosphatase enzyme which is found in saliva, in order to generate the peroxymonophsophate anion ($PO_5^{-3}$) which is slowly hydrolyzed to hydrogen peroxide and orthophosphate; the rate of peroxymonophosphate hydrolysis being slow and directly proportional to the phosphatase concentration. Extremely low phosphatase concentration can continue to generate $PO_5^{-3}$ over a prolonged period of time, e.g., several months. Thus, it is apparent that the substantivity of the peroxydiphosphate compound to the oral surfaces, and the continuous supply of phosphatase in the saliva provides for long lasting odor inhibition in the oral cavity. It has been found that a concentrations of about 0.01 to about 3% potassium peroxydiphosphate in oral compositions provides for optimum inhibition of volatile sulfur compound (VSC) formation.

Aqueous solutions of tetrapotassium peroxydiphosphate in concentrations ranging from 0.05 to 3% were tested in an in vitro system consisting of whole human saliva, L-cysteine as substrate, and incubated for periods ranging from 3 hours to 24 hours in an airtight container. After the periods of incubation, the headspace VSC were determined instrumentally using the GC-flame photometric technique, and also organoleptically (sensory evaluations). Equivalent concentrations of hydrogen peroxide were also tested. The results showed excellent inhibition by the tetrapotassium peroxydiphosphate by 100% supression of VSC formation and the absence of odor, even up to 24 hours of incubation of saliva system. The hydrogen peroxide, on the other hand, was less effective at lower concentrations after 24 hours of incubation.

At 3% concentration, both potassium peroxydiphosphate and $H_2O_2$ gave 100% VSC inhibition; whereas, at 0.75% concentration and after 24 hours incubation, the potassium peroxydiphosphate gave 93% VSC inhibition as against 50% VSC inhibition for $H_2O_2$. A 3% potassium peroxydiphosphate composition, after one month of aging and 24 hours of incubation, gave 70% effectiveness against VSC formation.

The peroxydiphosphates are commercially known and have been used in the prior art as a source for the generation of peroxymonophosphate, which is useful in germincidal, bleaching, dyeing, and metal detoxication processes as disclosed in U.S. Pat. No. 3,666,399, wherein the controlled generation of the peroxymonophosphate from the peroxydiphosphate is obtained in the persence of a phosphatase enzyme. U.S. Pat. No. 3,649,159 utilizes the peroxydiphosphate compound together with an oxidation dye to improve the coloring of hair or other keratinous substances. U.S. Pat. No. 3,649,158 uses the peroxydiphosphate together with alkaline hydrogen peroxide, to improve the bleaching of textile fabrics. However, the use of the peroxydiphosphate in oral compositions to inhibit the formation of volatile sulfur compounds, and thereby control mouth odor, is novel. It has been observed that the peroxydiphosphates are particularly effective in controlling mouth odor as a non-staining, non-antimicrobial mouth odor inhibitor.

The peroxydiphosphate salts are typically incorporated in oral preparations in effective amounts up to about 5% by weight, e.g., 0.01-5%, preferably 0.01-3%, and most preferably 0.075-3% by weight of the oral preparation. Typically, the oral preparation is a dentifrice, such as dental cream, tablet or power containing a dental vehicle.

The vehicle, often referred to as a dental vehicle contains liquids and solids. In general, the liquid comprises water and/or a humectant such as glycerine, sorbitol, propylene glycol or polyethylene glycol 400 including suitable mixtures thereof. It is usually advantageous to use a mixture of both water and one or two humectants. The total liquid content is generally about 20-90 percent by weight of the vehicle. In transparent and translucent vehicles, the liquid content of the toothpaste may be about 20-90 percent by weight, while in opaque vehicles the total liquid content is usually about 20-50 percent by weight. The preferred humectants are glycerine and sorbitol. Typically clear, that is transparent or tranelucent, vehicle contains 0-80 percent by weight of glycerine, about 20-80 percent by weight of sorbitol and about 20-80 percent by weight of water. Opaque vehicles typically contain about 15-35 percent by weight of glycerine and about 10-30 percent by weight of water.

The solid portion of the vehicle is a gelling agent. In the instant invention the gelling agent includes alkali metal carboxymethyl cellulose in amount of at least about 0.25 percent by weight of the vehicle. Additional gelling agents may also be present. Gelling agents which may be additionally present include viscarin, gelatin, starch, glucose, sucrose, polyvinyl pyrollidone, polyvinyl alcohol, gum tragacanth, gum karaya, hydroxy propyl cellulose, methyl cellulose, carboxyethyl cellulose, sodium alginate. Laponite CP or SP, which are each synthetic inorganic complex silicate clays sold under trademark by Laporte Industries. Ltd., and magnesium aluminum silicate gel. The solid portion or gelling agent of the vehicle is typically present in amount of about 0.25-10 percent by weight of the toothpaste and preferably about 0.5-8 percent by weight. Alkali metal carboxymethyl cellulose includes the lithium, sodium and potassium salts.

Any suitable substantially water-insoluble polishing agent may be added to the gel vehicle. There is a relatively large number of such materials known in the art. Representative materials include, for example, dicalcium phosphate, tricalcium phosphate, insoluble sodium metaphosphate, aluminum hydroxide, magnesium carbonate, calcium carbonate, calcium pyrophosphate, calcium sulfate, bentonite, etc., including suitable mixtures thereof. It is preferred to use the water-insoluble phosphate sodium metaphosphate and/or a calcium phosphate, such as dicalcium phosphate dihydrate. In general, these polishing agents will comprise a major proportion by weight of the solid ingredients. The polishing agent content is variable, but will generally be up to about 75 percent by weight of the total composition, generally about 20-75 percent; although, as indicated below, even lower amounts of polishing agent can be employed.

Any suitable surface-active or detersive material may be incorporated in the gel vehicle. Such compatible materials are desirable to provide additional detersive, foaming and antibacterial properties depending upon the specific type of surface-active material and are selected similarly. These detergents are water-soluble organic compounds usually, and may be anionic, non-ionic, or cationic in structure. It is preferred to use the water-soluble non-soap or synthetic organic detergents, usually. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropanesulfonate) and the like.

The various surface-active materials may be used in any suitable amount, generally from about 0.05 to about 10 percent by weight, and preferably from about 0.5 to 5 percent by weight of the dentifrice composition.

It is a further embodiment of the present invention to use the substantially saturated higher/aliphatic acyl amides of lower aliphatic amino carboxylic acid compounds, such as those having 12 to 16 carbons in the acyl radical, and as more particularly described in U.S. Pat. No. 2,689,170 issued Sept. 14, 1954. The amino acid portion is derived generally from the lower aliphatic satuated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine, and sodium N-lauroyl glycine and alanine. For convenience herein, reference to "amino carboxylic acid compound", "sarcoside", and the like refers to such compounds having a free carboxylic group or the water-soluble carboxylate salts.

Various other materials may be incorporated in the vehicles of this invention. Examples thereof are preservatives, silicones, chlorophyll compounds, ammoniated materials such as urea, diammonium phosphate and mixtures thereof, materials which can increase contrast with the particles, such as zinc oxide or titanium dioxide and other constituents. These adjuvants are incorporated in the instant compositions in amounts which do not substantially adversely affect the properties and characteristics suitably selected and used in proper amount depending upon the particular type of preparation involved.

Antibacterial agents may also be employed in the gelled vehicles of the instant invention. Typical antibacterial agents include:

$N^1$-(4-chlorobenzyl)-$N^5$-(2,4-dichlorobenzyl) biguanide;

p-chlorophenyl biguanide;

4-chlorobenzhydryl biguanide;

4-chlorobenzhydrylguanylurea;

N-3-lauroxypropyl-N-p-chlorobenzylbiguanide;

1,6-di-p-chlorophenylbiguanide hexane; 1-(lauryldimethylammonium)-8-(p-chlorobenzyldimethylammonium) octane dichloride;

5,6-dichloro-2-guanidinobenzimidazole;

$N^1$-p-chlorophenyl-$N^5$-laurylbiguanide;

5-amino-1,3-bis(2-ethylhexyl)-3-methylhexahydro pyrimidine; and their non-toxic acid addition salts.

The antibacterial agent, when present, is employed in amounts of about 0.1-5 percent by weight, preferably about 0.05-5 percent.

Any suitable flavoring or sweetening materials may be employed in formulating a flavor for the compositions of the present invention. Examples of suitable flavoring constituents include the flavoring oils, etc., oils of spearmint, peppermint, wintergreen, sassafras, clove, sage, eucalyputs, marjoram, cinnamon, lemon and orange, as well as sodium methylsalicylate. Suitable sweetening agents include sucrose, lactose, maltose, sorbitol, sodium cyclamate and saccharine. Suitably, flavor and sweetening agent may together comprise from about 0.01 to 5 percent or more of the compositions of the instant invention.

A fluorine-containing compound having a beneficial effect on the care and hygiene of the oral cavity, e.g., diminution of enamel solubility in acid and protection of the teeth against decay may also be incorporated in the gelled vehicle. Examples thereof includes sodium fluoride, stannous fluoride, potassium fluoride, potassium stannous fluoride ($SnF_2$—KF), sodium hexafluorostannate, stannous chlorofluoride, sodium fluorozirconate, and sodium monofluorophosphate. These materials, which disassociate or release fluorine-containing ions in water, suitably may be present in an effective but nontoxic amount, usually within the range of about 0.01 to 1 percent by weight of the water-soluble fluorine content thereof.

The oral preparation may also be a liquid such as mouth rinse which typically contains 20-99% by weight of an aqueous lower aliphatic alcohol, preferably having about 1-30% by weight alcohol such as ethanol, n-propyl, or isopropyl alcohol. The flavors most desirable in mouthrinse formulations in terms of stability and compatibility include thymol, eugenol, creosol, and methyl salicylate.

Such oral preparations are typically applied by brushing the teeth or rinsing the oral cavity for 30-90 seconds at least once daily. Typical oral preparations of the invention which can be applied in this manner are set forth below.

EXAMPLE 1

Dental Cream

| | % |
|---|---|
| Tetrapotassium peroxydiphosphate | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80-Polyoxyethylene (20 moles ethylene oxide) sorbitan monooleate.

EXAMPLE 2

Mouthwash

| | % |
|---|---|
| Tetrapotassium peroxydiphosphate | 3.0 |
| Ethyl alcohol | 15.0 |
| Non-ionic detergent (Pluronic F-108)* | 2.0 |
| Glycerol | 10.0 |
| Flavor | 0.4 |
| Sodium saccharin | 0.03 |
| FD&C color (0.1%) | 0.6 |
| Water q.s. | 100 |

*A polyalkene oxide block polymer.

This mouthrinse formulation was found to be effective in the inhibition of VSC formation even after two months of aging at room temperature. An incubated saliva system treated with this mouthwash resulted in the total absence of odor. However, a mouthwash containing hydrogen peroxide proved to be unstable.

EXAMPLE 3

0.75% tetrapotassium peroxydiphosphate was substituted for the 3% peroxydiphosphate and the water adjusted accordingly, with substantially the same reduction in VSC formation and the elimination of mouth odor.

An effective amount, e.g., 0.01 to about 10% by weight of the peroxydiphosphate salt may also be incorporated by dry mixing with an inert carrier or dissolving in a suitable vehicle in the formulation of chewing gums and lozenges. Similarly, the peroxydiphosphate salt may also be incorporated into a mouth spray. A typical lozenge formula contains the following ingredients, in percent by weight, based on the weight of the total formulation:

| | | | |
|---|---|---|---|
| 75% | to | 98% | Sugar |
| 1% | to | 20% | Corn Syrup |
| .1% | to | 1% | Flavor oil |
| 0% | to | .03% | Colorant(s) |
| .1% | to | 5% | Tableting Lubricant |
| .2% | to | 2% | Water |
| .01% | to | 10% | Peroxydiphosphate Salt |

Sugarless pressed candy may also be formulated to include the peroxydiphosphates of this invention. For products of this type, which usually contain powdered sorbitol instead of sugar, synthetic sweeteners are mixed with the powdered sorbitol and flavor (s), colorant(s) and a tablet lubricant are then added. The formula is introduced into a tablet machine to shape the final product. A typical sugarless pressed candy contains the following ingredients, in percent by weight, based on the weight of the total formulation:

| | | |
|---|---|---|
| 98% to | 99.5% | Sorbitol |
| .1% to | .9% | Flavor(s) |
| 0% to | .02% | Synthetic Sweeteners |
| 0% to | .03% | Colorant(s) |
| .05% to | 1% | Tableting Lubricant |

Obviously many variations of the above described procedures may be used to prepared pressed candies.

A typical chewing gum may contain the following ingredients, in percent by weight based on the weight of the total gum formulation:

| Ingredients | Weight Percent |
|---|---|
| Gum Base | From about 10% to about 40% |
| Sucrose | From about 50% to about 75% |
| Corn Syrup or Glucose | From about 10% to about 20% |
| Flavor Material | From about 0.4% to about 5% |
| Peroxydiphosphate Salt | From about .01% to about 10% |

An alternate chewing gum formulation is as follows:

| Ingredients | Weight Percent |
|---|---|
| Gum Base | From about 10% to about 50% |
| Binder | From about 3% to about 10% |
| Filler (Sorbitol, Mannitol or combinations thereof) | From about 5% to about 80% |
| Artificial Sweetener and Flavor | From about 0.1% to about 5% |
| Peroxydiphosphate Salt | From about .01% to about 10% |

In certain sugarless gums, there is used as the binder ingredient a solution of sorbitol in water containing from about 10% to about 80%, preferably from about 50 to about 75% by weight of sorbitol in $H_2O$. In others, there is used a gum acacia-in-water system containing from about 30 to about 60%, preferably from about 45 to about 50% by weight of gum acacia powder.

The above chewing gum formulations are exemplary only. Many additional formulations are described in the prior art, and in carrying out this invention, such formulations can be employed. It is also possible to prepare an acceptable chewing gum product containing a gum base, flavoring material and peroxydiphosphate salt according to the teaching of this invention.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutylene-isoprene copolymer, paraffin, petroleum wax, polyethylene, polyisobutylene, polyvinylacetate, etc.; plasticizers such as lanolin, stearic acid, sodium stearate, potassium stearate, etc.

Any of the alkali metal peroxydiphosphates or their corresponding acid salts that are water-soluble to the extend of about 0.001 weight percent can be used in the composition of this invention. Examples of these are potassium peroxydiphosphate ($K_4P_4O_8$), lithium peroxydiphosphate ($Li_4P_2O_8$) sodium peroxydiphosphate ($Na_4P_2O_8$), tripotassium monosodium peroxydiphosphate ($K_3NaP_2O_8$), dipotassium disodium peroxydiphosphate ($K_2Na_2P_2O_8.2H_2O$), monopotassium trisodium peroxydiphosphate ($KNa_3P_2O_8$), monopotassium monosodium dihydrogen peroxydiphosphate ($KNaH_2P_2O_8$), trilithium monopotassium peroxydiphosphate ($Li_3KP_2O_8$), dilithium dipotassium peroxydiphosphate ($Li_2K_2P_2O_8$), monolithium tripotassium peroxydiphosphate ($LiK_3P_2O_8$), trilithium monosodium peroxydiphosphate ($Li_3NaP_2O_8$), dilithium disodium peroxydiphosphate ($Li_2Na_2P_2O_8$), monolithium trisodium peroxydiphosphate ($LiNa_3P_2O_8$), monolithium monosodium dihydrogen peroxydiphosphate ($LiNaH_2P_2O_8$), monolithium monopotassium dihydrogen peroxydiphosphate ($LiKH_2P_2O_8$), and the acid salts of group 2 metals such as barium dihydrogen peroxydiphosphate ($BaH_2P_2O_8$), and calcium dihydrogen peroxydiphosphate ($CaH_2P_2O_8$).

A preferred ingredient of instant composition is a non-ionic organic surfactant which provides increased prophylactic action, assists in achieving thorough and complete dispersion of instant compositions throughout the oral cavity and renders instant composition more cosmetically acceptable. The non-ionic surfactant imparts to the composition detersive and foaming properties, as well as maintains the flavoring materials in solution (i.e., solubilizes flavor oils). In addition, the non-ionics are completely compatible with the peroxydiphosphates of this invention, thereby providing for a stable, homogeneous composition of superior mouth odor control.

The non-ionic organic surface active compounds which are contemplated are commercially known and comprise water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, sulphoamides, etc. The ethylene oxide condensates with higher-alkyl phenols represent a preferred class of non-ionic compounds. Usually the hydrophobic moiety should contain at least about 6 carbon atoms, and preferably at least about 8 carbon atoms, and may contain as many as about 50 carbon atoms or more. The amount of alkylene oxide will vary considerably, depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrohobe may be employed. While ethylene oxide is the preferred and predominating oxyalkylating reagent, other lower alkylene oxides such as propylene oxide, butylene oxide, and the like, may also be used or substituted in part for the ethylene oxide. Other non-ionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other non-ionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of non-ionic products are the oxyalkylated higher aliphatic alcohols. The fatty alcohols should contain at least 6 carbon atoms, and preferably at least about 8 carbon atoms. The most preferred alcohols are lauryl, myristyl, cetyl, stearyl and oleyl alcohols and the said alcohols should be condensed with at least about 6 moles of ethylene oxide, and preferably about 10 to 30 moles of ethylene oxide. A typical non-ionic product is oleyl alcohol condensed with 15 moles of ethylene oxide.

The amount of non-ionic may generally be varied from about 0.2–3.0% by weight of the total formulation, depending on the specific nature of the non-ionic utilized, as well as on the amounts and nature of the other ingredients in the oral formulation.

Although this invention has been described with reference to specific examples, it will be apparent to one skilled in the art that various modifications may be made thereto which fall within its scope.

What is claimed:

1. An improved oral composition containing a peroxydiphosphate salt as an effective non-antimicrobial, non-staining mouth odor inhibitor.

2. A composition in accordance with claim 1, wherein the mouth odor inhibitor constitutes about 0.01–3% by weight of the composition.

3. An oral composition in accordance with claim 1, which also contains a non-ionic surfactant.

4. An oral composition in accordance with claim 1, wherein the mouth odor inhibitor is tetrapotassium peroxydiphosphate.

5. A method of preventing and controlling mouth odor which comprises applying the composition of claim 1 to the oral cavity, wherein the peroxydiphosphate is activated by the salivary phosphatases to form the peroxymonophosphate anion which slowly and continuously generate hydrogen peroxide which deodorizes the oral cavity.

6. A method in accordance with claim 5, which comprises brushing the teeth with a dental cream.

7. A method in accordance with claim 5, which comprises brushing the teeth with an oral powder.

8. A method in accordance with claim 5, which comprises rinsing the oral cavity with an aqueous-alcoholic mouthwash.

9. In the method of preventing and controlling mouth odor by treating the oral cavity with the composition of claim 1, the improvement which comprises having present in the oral composition from 0.01 to 3% of a peroxydiphosphate salt which reacts on contact with salivary phosphatases to give the peroxymonophosphate anion which slowly generates hydrogen peroxide and eliminates the odoriferous substances in the oral cavity.

* * * * *